United States Patent [19]

Mendelson et al.

[11] 4,082,095
[45] Apr. 4, 1978

[54] STOMACH PUMP

[75] Inventors: Barry Mendelson, Spring Valley, N.Y.; Stephen A. Denman, Dayton, Ohio

[73] Assignee: Barry Mendelson, Spring Valley, N.Y.

[21] Appl. No.: 816,539

[22] Filed: Jul. 18, 1977

Related U.S. Application Data

[63] Continuation of Ser. No. 621,061, Oct. 9, 1975, abandoned.

[51] Int. Cl.² ............................................. A61M 1/00
[52] U.S. Cl. ..................... 128/235; 128/273; 128/274
[58] Field of Search ................. 128/230–238, 128/273, 274, 224, 276–278, 214 R, 214 B; 222/387, 486; 417/442; 73/425.6; 137/625.46

[56] References Cited

U.S. PATENT DOCUMENTS

| | | | |
|---|---|---|---|
| 1,578,383 | 3/1926 | Bayles et al. | 128/274 X |
| 1,585,628 | 5/1926 | Pfarre | 128/214 B X |
| 1,633,074 | 6/1927 | DeMott | 128/274 X |
| 1,710,540 | 4/1929 | Hollander | 128/274 X |
| 1,948,388 | 2/1934 | Liberson | 128/234 |
| 2,077,774 | 4/1937 | Rudder | 128/214 B |
| 2,538,215 | 1/1951 | Stack | 128/231 X |
| 2,628,746 | 2/1953 | James | 222/486 |
| 2,812,765 | 11/1957 | Tofflemire | 128/276 |
| 2,842,124 | 7/1958 | James | 128/214 B |
| 2,908,293 | 10/1959 | Johnson | 137/625.46 |
| 3,048,192 | 8/1962 | Murphy, Jr. | 128/274 X |
| 3,157,201 | 11/1964 | Littmann | 128/214 B X |
| 3,344,785 | 10/1967 | Hamilton | 128/214 B |
| 3,780,736 | 12/1973 | Chen | 128/231 |
| 3,834,372 | 9/1974 | Turney | 128/274 X |

FOREIGN PATENT DOCUMENTS

| | | | |
|---|---|---|---|
| 569,09 | 1/1933 | Germany | 128/234 |
| 240,189 | 4/1926 | United Kingdom | 128/214 B |

Primary Examiner—John D. Yasko
Attorney, Agent, or Firm—Martin G. Raskin

[57] ABSTRACT

Intubation apparatus in which a syringe, valve elements and other components of a stomach pump or the like are comprised in a unitary assembly made for a one-time or limited use. A single valve element controls flow of fluids to and from the syringe and is adjustable in indexing motions to place the syringe variously in communication with a tube to be inserted in a body opening and with tubes leading to a container of irrigating fluid, a waste container and a sample container.

17 Claims, 14 Drawing Figures

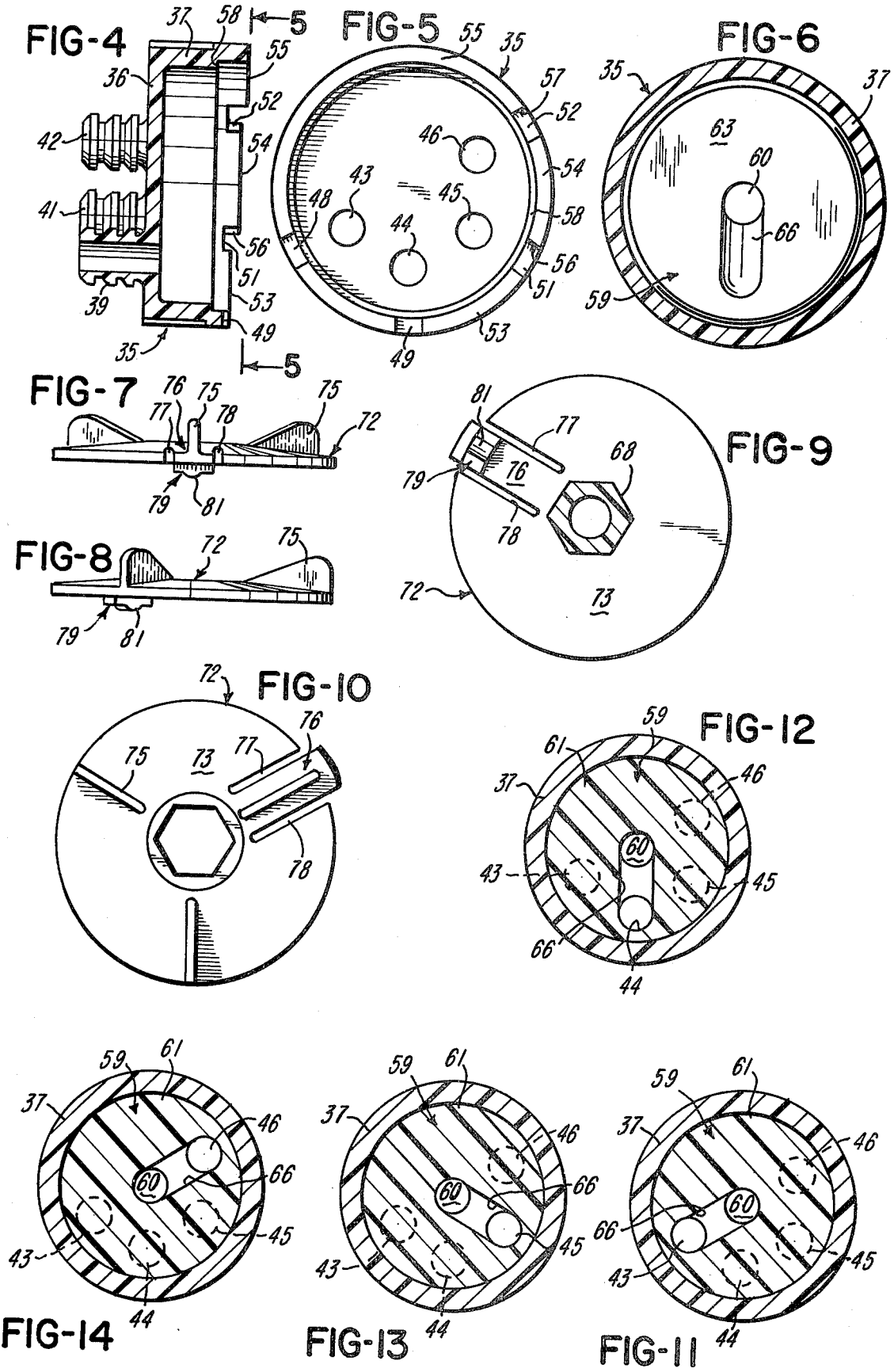

STOMACH PUMP

This is a continuation of application Ser. No. 621,061, filed Oct. 9, 1975, now abandoned.

BACKGROUND OF THE INVENTION

This invention relates to intubation apparatus and particularly to stomach pumps. In the prior art, stomach pumps have assumed the form of machine systems. They are costly, complex in structure and operation and must be carefully maintained to assure that they will be sanitary and in good working order when required to be used. Relatively high investment expense and storage requirements limit the number of pumps that can practicably be kept on hand. The pumps are portable only in a narrow sense and cannot be used apart from an energizing power source. Accordingly, stomach pumps as heretofore known inadequately serve the needs for which they have been developed. Concepts of irrigation of body cavities involving use of a directional valve have heretofore been known. They do not, however, contemplate a unitary expendable system; particularly one involving the combination of a syringe and adjustable valve means.

SUMMARY OF THE INVENTION

An intubation apparatus or more particularly a stomach pump according to the present invention is a simple, easily used system, made so inexpensively that it may be supplied as a disposable or expendable device of limited or one-time use. It is hand controlled and hand powered. It is compact and easily stored and so can be kept on hand in quantity wherever its use would likely be or might be required. According to an illustrative embodiment of the invention, a stomach pump is made of lightweight, inexpensive material and includes an integrated syringe and valve assembly, the latter being multi ported and having tubes attached thereto and individually communicating through respective ports with the syringe. One of the tubes is adapted to be inserted in a body opening. The others extend to container bags which may be a part of the disposable pump system. The bags include a sample bag receiving a specimen of stomach fluids for laboratory examination. The valve assembly comprises a multi ported valve body, a valve rotor adjustable relatively to the body selectively to intercommunicate the syringe with individual ports, and a detenting arrangement whereby the valve rotor is held yieldingly in set positions of adjustment. The detenting arrangement requires a separate manual intervention to place the syringe in communication with the tube leading to the sample bag. The likelihood is reduced thereby of fluids inadvertently being directed to the sample bag tube at a time when the bag is removed.

An object of the invention is to provide a stomach pump made expendable to obviate problems of initial expense, maintenance and sterilization.

Another object of the invention is to provide a stomach pump usable independently of outside power sources and simple in its construction and operation.

A further object of the invention is to provide a stomach pump involving a novel combination of syringe and valve, the valve including a valve element accessible for adjustment to communicate the syringe selectively with a body insert tube and with tubes leading to fluid supply, waste and sample containers.

Still another object of the invention is to provide a detenting and indexing mechanism for the valve element including an arrangement requiring a separate manual intervention to communicate the syringe with the sample bag.

A still further object of the invention is to provide a stomach pump made in inexpensive, unitary package form so as to be readily available for use as a disposable article of manufacture.

With the above and other incidental objects in view as will more fully appear in the specification, the invention intended to be protected by Letters Patent consists of the features of construction, the parts and combinations thereof, and the mode of operation as hereinafter described or illustrated in the accompanying drawings, or their equivalents.

Referring to the accompanying drawing wherein is shown one but obviously not necessarily the only form of embodiment of the invention, FIG. 1 is a view in side elevation of a stomach pump system according to the illustrated embodiment of the invention, projecting tube elements being broken away;

FIG. 4 is a longitudinal sectional view of the valve body;

FIG. 5 is a view of the open end of the valve body;

FIG. 6 is a view in cross section, taken substantially along the line 6—6 of FIG. 3 particularly illustrating the base end of the valve rotor;

FIG. 7 is a side view of the valve operating disc;

FIG. 8 is a further view of the valve operating disc;

FIG. 9 is a view in cross section taken substantially along the line 9—9 of FIG. 3;

FIG. 10 is a view in cross section taken substantially along the line 10—10 of FIG. 3; and FIGS. 11, 12, 13 and 14 are diagrammatic views indicating the connections effected in the different positions of adjustment of the valve rotor.

Like parts are indicated by similar characters of reference throughout the several views.

Figure 1:
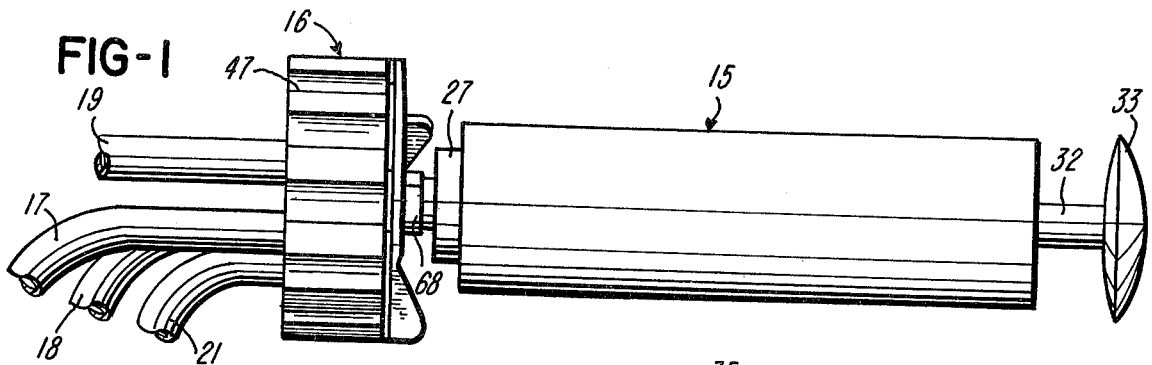

Referring to the drawings, intubation apparatus according to the illustrated embodiment of the invention takes the form of a system providing a stomach pump. It is a compact, unitary assembly which may be simply packaged and stored to be conveniently available for use on an emergency basis as well as at usual treatment locations.

The system includes a syringe 15, a valve means 16, and a plurality of tubes 17, 18, 19 and 21 leading from the valve means. Container bags 22, 23 and 24 receive and are releasably coupled to outer free ends of the tubes 17, 18 and 19. Tube 21 is adapted to be communicated through a body orifice with a cavity in a living body. As will be seen, the valve means 16 incorporates an adjustable valve member whereby the syringe 15 may be selectively placed in communication with the tubes 17, 18, 19 and 21. This valve member is provided with simple but effective indexing means which enable a safe and sure achievement of a desired sequence of operation.

The syringe 15 comprises a tube defining a hollow cylinder 25, one end of which is closed by a bearing disc 26. The opposite end of cylinder 25 is formed to provide it with a reduced diameter tubular tip portion 27, the interior wall of which is formed to embody screw threads 29.

A piston 31 is contained by and bears for reciprocation on the interior wall of the cylinder 25 between the bearing disc 26 and opposed, longitudinally spaced, shoulder 20 created interiorly of the cylinder 25 in the formation of the tip 27. A piston rod 32 attaches at one end to the piston 31 and extends centrally and axially of the chamber defined by the cylinder 25 to project through and bear in the disc 26 and have its projected extremity position outside the cylinder to the end thereof opposite the tip 27. The projected extremity of the rod 32 is provided with an enlarged heat portion 33. The latter is formed on or suitably attached to the outermost end of rod 32 to provide it with means facilitating a manual reciprocation thereof in a manner believed obvious. The parts of the syringe are made of a light weight, inexpensive plastic material. Moreover, heat or sonic welding is used to join the parts, one to the other, as in the case of mounting and connecting disc 26 to the cylinder 25 and attaching the rod 32 to piston 31. As will be seen in the drawings, the periphery of the piston 31 is formed with circumferential and longitudinally spaced recesses in each of which it is seated an elastomeric or like O-ring 34 which projects outwardly of the piston to bear on and form a seal with the inner wall of the cylinder 25 in the course of a reciprocating movement of the piston 31.

Figure 2:
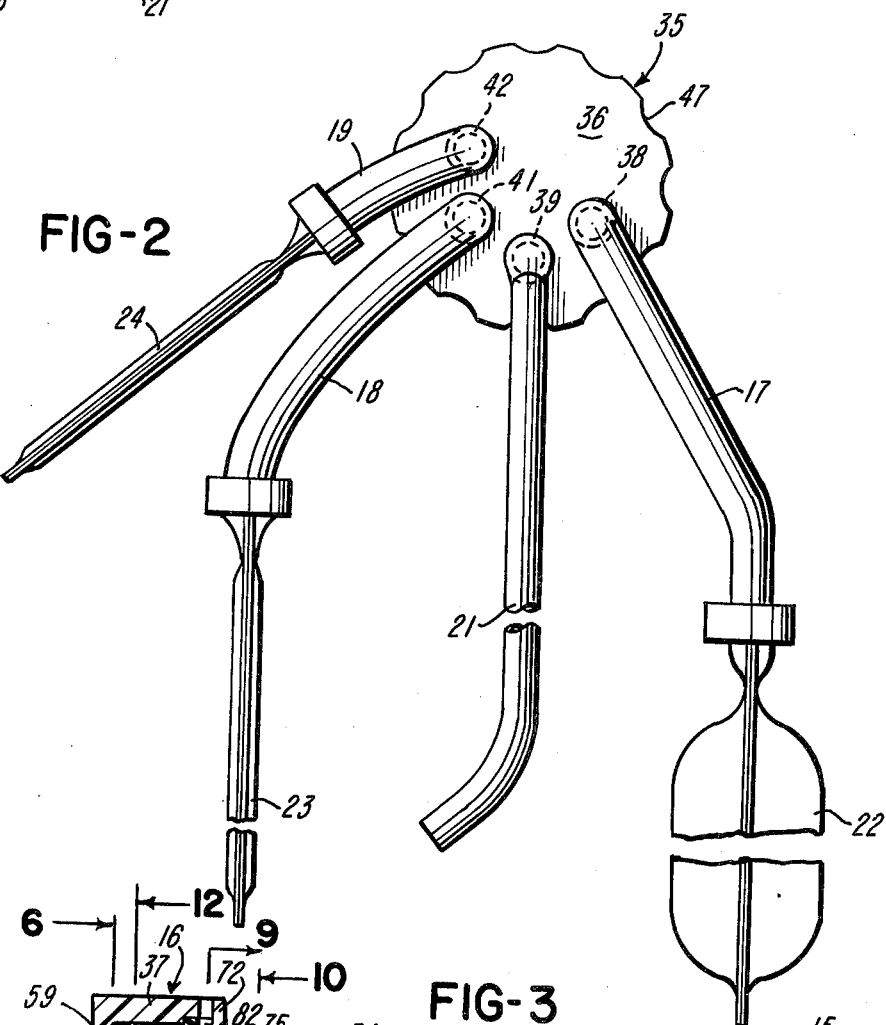
FIG. 2 is an end view of the system of FIG. 1, the tubes thereof being shown as attached to appropriate containers to provide for its application as a stomach pump.
Figure 3:
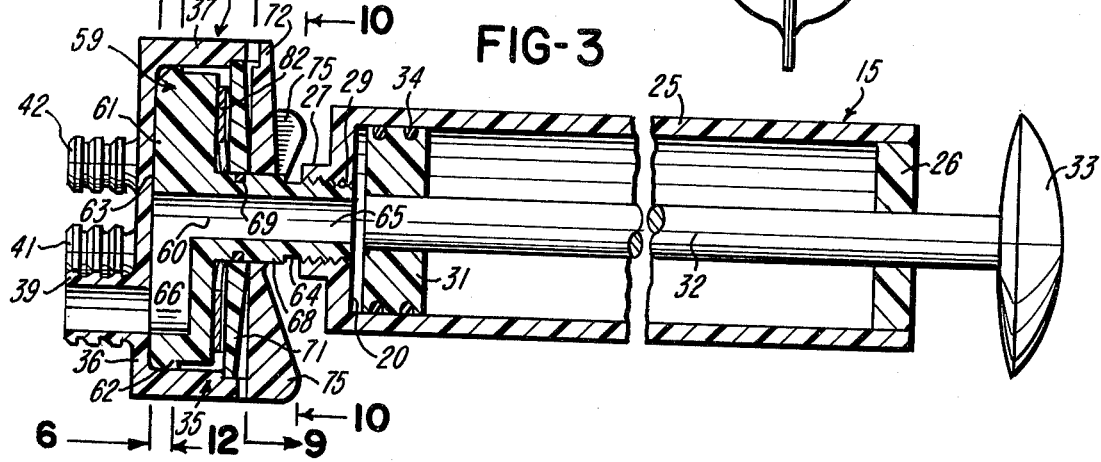
FIG. 3 is an enlarged view in longitudinal section of a syringe and valve combination as comprised in the system of FIGS. 1 and 2.

The valve means 16 includes a cup-shaped valve body 35 (FIGS. 4 and 5) having a base wall portion 36 rimmed by a peripherally and perpendicularly projected wall structure 37. Projected perpendicular to and outwardly from what may be regarded as the outermost face of the base wall portion 36 is a series of tubular protuberances 38, 39, 41 and 42 (FIG. 2). These protuberances are so positioned as to be spaced along an arcuate path and the passages which they define are respectively open to and communicate with ports 43, 44, 45 and 46 formed in the base wall portion 36 to open to the interior of the cup-shaped valve body 35. Each of the protuberances 38, 39, 41 and 42 are provided with a plurality of longitudinally spaced, radially projected bands formed integral therewith to facilitate a firm sealing grip thereof by an applied plastic or rubber hose such as the tubes 17, 18, 19 and 21.

The outer surface of the wall structure of the valve body 35 is externally fluted to provide it with a series of longitudinally extending, circumferentially spaced indentations 47 which facilitate the gripping of the body by a hand. The end of the wall structure 37 remote from the base 36 of the valve body 35 is formed to include a series of notches 48, 49, 51 and 52 so located and so spaced from one another as to respectively radially align with the ports 43, 44, 45 and 46. Also, the projected end of the wall structure 37 of the valve body 35, remote from its base portion 36, is structurally characterized by a stepped configuration. This provides that segments of the wall structure identified by numerals 53, 54 and 55 are of respectively different heights or lengths, segment 53 having the shortest and segment 55 having the greatest length or height. The stepping of the projected end of the wall structure 37 provides an axially oriented shoulder 56 forming a line of demarcation between the segments 53 and 54 and a shoulder 57 similarly forming a line of demarcation between the segments 54 and 55. Attention is directed to the fact that a shallow counterbore 58 is provided in what may be regarded as the open end of the cup-like body 35.

Valves means 16 further includes a valve rotor 59 which is received with a sliding fit in the interior of the valve body 35. The rotor 59 includes a disc-like body portion 61 the base 63 of which seats in generally coextensive bearing relation to the interior surface of the base portion 36 of the body 35. Immediately adjacent its base surface the circular periphery of the body of the rotor 59 includes an annular projection 62 the peripheral surface of which positions in bearing relation to the interior wall surface of the wall structure 37. The outer periphery of the body of the rotor 59 is otherwise relieved to position in a generally spaced parallel relation to the wall structure 37. It will accordingly be seen that there is a minimal bearing relation between the wall structure 37 and the contained body portion of the rotor 59 which facilitates an easy rotation of the rotor as and when required. Formed in the base surface 63 of the rotor body 61 is a radial slot or groove 66. The radially innermost end of the slot 66 aligns with an aperture 60 forming a passage positioned centrally and extending axially of the rotor body 61 which communicates at one end with the groove 66 and at the other end with an axially aligned passage 65 in a tubular stem 64. The latter is formed integral with and projected perpendicular to the rotor body portion 61, at the end thereof remote from its base surface 63. The stem 64 is accordingly centered with reference to the rotor body portion 61 and the valve body 35. The stem 64 is elongated to project, to a substantial extent, beyond the projected limits of the valve body wall structure 37. The outermost surface of the projected extremity of the stem 64 is threaded for the coupling thereof in threaded engagement with the threads 29 formed interiorly of the tip 27 of the cylinder 25.

Seated to the outermost surface of the rotor body portion 61, in concentric spaced relation to the root of the stem 64, is an annular wave-formed spring 82. The spring 82 is contained in place by the application of an annular cover plate 71 seated in the counterbore 58 in the open end of the valve body 35. The outer peripheral portion of the cover disc 71 is suitably welded in connection with the wall structure 37, while its inner periphery immediately surrounds and bears on the outer surface of the stem 64, an O-ring 69 being disposed therebetween. This seal permits a bearing rotation of the stem 64 in and with reference to the cover disc which permits the ready rotation of the rotor 59 of which the body 61 and the stem 64 are integral parts. It will be seen that the purpose and function of the wave spring 82, confined as described, is to achieve a balanced rotation of the rotor body 61 in the valve body 35 and to hold the rotor in place, once the position thereof is set for achieving a particular function.

Further comprised in the valve means 16 is a disc shaped valve operating disc 72. Immediately outward of the cover disc 71 the outer peripheral surface of the stem 64 of the rotor 59 is circumferentially provided with flats giving it a generally hexagonal cross-sectional configuration. This portion of the stem 64 is identified by the numeral 68. The disc 72 includes a central aperture having a hexagonal configuration designed to be complementary to the hexagonal configuration of the stem portion 68. This permits, on the assembly of the valve means 16, that the disc 72 be slipped over the threaded end of the stem 64 to have the hexagonal apertured portion thereof fit about and with the portion 68 of the stem, dictating thereby that any turning of the disc 72 will produce a turning of the stem 64 and thereby of the rotor 59. As so positioned, the disc 72 is welded to the stem to normally dispose in an immediate end capping relation to the projected stepped extremity of the wall structure 37. The disc 72 is generally flat and has on what may be regarded as its outermost face a plurality of radially oriented, perpendicularly projected ribs 75. One of the ribs 75 is centered between parallel slots 77 and 78 formed in the periphery of the flat body portion 73 of the disc 72. This produces in the body portion 73 what may be regarded as the radial flexible tab 76 capable of resiliently flexing in respect to the remainder of the disc 72. The tab 76 is radially elongated with reference to the remainder of the body 73 so its outermost end projects beyond the periphery of the remainder of the disc 72. In this respect, the projected end portion of the tab 76 also projects radially outward of the wall 37 of the cup-shaped valve body which it caps. It will be seen that this facilitates a manual lifting and flexing of the tab 76 for purposes which shall soon become obvious. On what may be considered the innermost side of the tab 76, in a position coincident and aligned with the adjacent underlying projected extremity of the wall structure 37 is a projected lug member 79, from the innermost surface of which further projects an arcuately configured protrusion 81. As will be seen, the protrusion 81 is designed to be selectively positioned in one of the notches 48, 49, 51 and 52 in an indexing procedure.

The disc 72 is preferably formed of plastic in a molding or like operation so that it may be insured that the tab 76 may be flexed as and when required.

By reason of its containment by the cover plate 71, the wave formed spring 82 serves to normally bias the base 63 of the rotor body 59 to seat to the base 36 of the cup-shaped valve body 35. This, in turn, causes that the outer peripheral part of the inner surface of the operator disc 72 to be biased to engage with the projected rim of the wall structure 37.

The tubes 17, 18, 19 and 21 are flexible hose-like members made of a suitably inert or corrosion resistant material which at their one end slip over and frictionally fit in sealing engagement with the respective protuberances 38, 41, 42 and 39. Clamps may be applied to further fix the tubes, if desired, but will normally not be necessary. The opposite ends of the tubes 17, 18 and 19 are respectively and appropriately attached to and sealingly engaged in or about the mouth defining openings to the respective containers 22, 23 and 24. The tube 22 is relatively elongated and has the free outer end thereof adapted to be inserted into a cavity of a living body through a body orifice.

The containers 22, 23 and 24 are preferably of thin, relatively inexpensive plastic material and provided thereby as expansible bags admirably suited to both provide economy and efficiency in their useful operation.

Sealing of the system and its respective parts is achieved, as and where required, by the application of suitable waterproof sealing compounds.

As described, the valve unit of the invention provides for a simple and easy coupling thereof to the cylinder 25 by effecting a threaded engagement of the stem 64 in the cylinder tip 27 in a manner believed obvious. In any case, the parts of the invention system may be easily, quickly and economically assembled by the fabricator or, if the same should be desired, at a place of use.

The unique valve means 16 as embodied in the invention assembly per se, has features which enhance the efficiency and sureness with which the system may function. Of course, it will be self-evident that the valve means 16 is admirably suited for use in other applications where it may serve like functions. Attention is directed to the fact that while the body portion 61 of the rotor 59 is contained in the housing provided by the valve body 35 and cover plate 71, the interposition of the biasing spring 82 as here provided enables not only a bias on the rotor body but a limited axial movement of the rotor within its housing which may be used to good advantage.

In use of the described apparatus as a stomach pump, the bag 22 is filled with a supply of suitable irrigating fluid and thus becomes a source of fluid which will be used to flush the stomach of a patient. The bag 23 will serve as a waste container while the bag 24, the application of which is optional, will serve as a sample container, that is a container into which a small amount or specimen of stomach fluids may be drawn off for laboratory analysis.

Prior to application of the system to the patient, the valve operating disc 72 will be manipulated through the medium of lever means which is provided by an extended portion of a rib 75 other than that on the tab 76 so as to rotate and adjust the rotor 59 to provide that the slot or groove 66 in the base 63 thereof will communicate the interior of the chamber defined by the cylinder 25, in advance of piston 31, with the opening 43 in the valve body 35. This has the effect of placing the irrigating fluid in the bag 22 in direct and open communication with the interior of the syringe the body of which is defined by the cylinder 25. This having been achieved, the free end of the tube 21 will be inserted by way of the patient's nostril, for example, so as to communicate the same with the contents of the patient's stomach.

In a stomach pumping cycle which follows, the piston assembly 31-33 of the syringe 15 will be retracted to apply suction to the contents of the bag 22. As a result, a charge of irrigating fluid is drawn interiorly of the syringe in advance of the piston 31. When the syringe is filled with irrigating fluid, the valve rotor 59 is turned to move the slot 66 out of communication with the opening 43 and into communication with the opening 44 in the valve body 35. This has the effect of disconnecting the syringe from the supply of irrigating fluid and connecting the irrigating fluid in the syringe with the tube 21. Upon the piston 31 being pressed inwardly of the cylinder 25, the irrigating fluid previously drawn into the cylinder is then forced into the stomach by way of the tube 21. The application of the fluid in this manner has a washing and diluting effect, the first with respect to the stomach and the other with respect to its contents. The piston rod assembly can then be retracted to draw stomach fluids intermingled with a small portion of the irrigating fluid, by way of the tube 21, into the syringe. When the syringe is filled with this mixture, primarily of stomach fluids, the valve rotor may be turned to place the contents of the syringe in communication with the valve opening 45 which leads to the waste container bag 23. On thrusting the piston assembly inwardly of the cylinder 25, the piston is effective to expel the syringe contents and drive it to the waste container in a manner believed obvious. This completes a full cycle of the system in respect to applying irrigating fluid to the contents of a stomach, and extracting a portion of the stomach contents and directing it to a waste container. The valve rotor may now be manually turned to once again communicate the interior of the syringe with the bag 22, thereby conditioning the system for a new sequence of the same operations. At any time it is desired that a sample of the stomach contents be extracted from the system, following the operation whereby the syringe is filled with a portion of the stomach contents of the patient, the valve rotor may be turned to align the slot 66 in the base of the body 61 thereof with the opening 46. Upon then pressing the piston assembly inwardly of the cylinder 25, the contents of the syringe are forced into the sample bag 24. On turning the valve rotor 59 to communicate the syringe with the irrigating fluid, one may then quickly remove the sample bag and direct the same to a laboratory for analysis of its contents.

The several positions in which the valve rotor may be placed in relation to the valve body are shown diagrammatically in FIGS. 11-14 of the drawings. As may be seen, FIG. 11 shows the position of the valve rotor when it is desired to communicate the syringe with the contents of the bag 22. FIG. 12 shows the position of the valve rotor in reference to the valve body during the time in which irrigating fluid is applied in and stomach contents are withdrawn from the patient's stomach. FIG. 13 shows the valve arrangement when the parts are in a position to direct stomach contents to the waste container while FIG. 14 illustrates the parts as set for directing a sample of the stomach contents to the sample bag 24.

It will be seen that the fluted exterior of the valve body 35 provides a means, where required, to facilitate a holding of the valve body with one hand while the rotor 59 is turned by manipulating the valve operator 72 with the other hand. The provision of the ribs 75 facilitate a finger tip control in the adjustment and readjustment of the position of the valve rotor.

As previously described, the notches 48, 49, 51 and 52 function cooperatively with the protrusion 81 embodied in the tab 76. As the valve operator disc 72 is turned in the course of the system operation, the protrusion 81 will selectively dispose in one of the notches in the projected underlying end of the wall structure 37 of the valve body 35. By such means, in the course of the rotation of the valve operator, one may selectively progress from one step in the cycle of operation of the stomach pump to the next with sureness. As the operator is turned the tab 76 will flex to displace the protrusion 81 from the notch in which it is set and the protrusion will be automatically biased into the next notch with which it aligns to indicate a proper setting for the next step in the pump operation. The flexing will be readily and positively sensed by the fingers of the manipulator. Thus, in the turning of the operator the protrusion 81 will provide for a controlled detented movement of the operator and thereby of the valve rotor. In any case, and in any setting, the protrusion 81 rests in the notch in which it is set in a manner to yieldingly maintain the rotor in its set position of adjustment.

Attention is directed to the fact that the construction of the valve body 35 is such as to place the openings 43, 44 and 45 in its base within a segmental area of the body occupied peripherally by the segment 53 of the wall structure 57 which has the least extent of projection from the base 36. This provides that in the cycle of operation of the operator 72 to move through a cycle of stomach pump operation, excluding use of the sample bag 24, the protrusion 81 will be riding from one notch to the other on the segment 53. If one would wish to turn the valve operator to a sample bag position, this could not be achieved without lifting the tab 76, since the lug 79 in so positioned that, on rotation of the operator in the direction of the notch indicating a position for sampling, it will engage the shoulder 56. This insures that the valve means cannot inadvertently be set to communicate the syringe with the sample bag 24. To achieve a sample positioning, the tab 76 must by physically lifted by its projected end portion to clear the lug 79 from the shoulder 56. When this occurs, the operator can then be advanced over the segment 54 to engage the next shoulder 57. In this position the lug and its protrusion 81 will bias into the notch 51 and thereby lodge in a position to communicate the slot 66 with the opening 46. Accordingly, the construction of the valve 16 is such to preclude inadvertent misoperation of the system as a stomach pump. It will be seen from the foregoing that the apparatus of the invention provides a self-contained disposable system for use as a stomach pump or the like. The apparatus embodies simple and economically formed elements the composition of which is such to relate them in a simple and safe manner to provide all the requirements for irrigating and draining a body cavity, as well as for sampling fluids therefrom. The apparatus requires no outside source of power nor does it require automatic or complicated indexing means. Not only is the package provided by the invention simply fabricated and economically achievable, its form is so compact as to enable handling, transport and storage easily and economically. Parts have been identified herein as being made primarily of a plastic material and such a construction is consistent and preferable to achieve the objective of a one time use, throw away product. Obviously, however, the parts may be made in any suitable manner and of any appropriate material as contemplated by the teachings of the present disclosure.

It should be obvious, of course, that in the particular embodiment of the invention here described the cylinder 25 and the stem 64 of rotor 59 are physically coupled. The coupling is such as to provide that as the valve operator 72 is turned, so is the syringe 15. By the same token the connection of the stem 64 to the tip 27 may be such to integrally connect the syringe to the rotor so they will move as one. In such event the syringe may per se be rotated with one hand while the body 35 is gripped by the other. In any case the lightweight, disposable, compact system of the invention facilitates a hand manipulation of the syringe-rotor structure which is easy and simple to achieve. The rotor could of course be mounted to have its stem in bearing rotatable engagement with the cylinder tip 25, but such is not preferred.

From the above description it will be apparent that there is thus provided a device of the character described possessing the particular features of advantage before enumerated as desirable, but which obviously is susceptible of modification in its form, proportions, detail construction and arrangement of parts without departing from the principle involved or sacrificing any of its advantages.

While in order to comply with the statute the invention has been described in language more or less specific as to structural features, it is to be understood that the invention is not limited to the specific features shown, but that the means and construction herein disclosed comprise but one of several modes of putting the invention into effect and the invention is therefore claimed in any of its forms or modifications within the legitimate and valid scope of the appended claims.

The embodiments of the invention in which an exclusive property as privilege is claimed are defined as follows:

1. Intubation apparatus comprising:
a syringe having an end portion including an opening communicating with the interior of said syringe, and
a valve assembly connected to said syringe end portion including a housing having a plurality of ports, a rotor member, said housing and rotor member being rotatably mounted with respect to each other; first means for automatically setting said housing and rotor member into a selected one of a first portion of a plurality of operating positions relative to each other solely by rotating said housing relative to said rotor member, said plurality of operating positions corresponding to said plurality of ports; means formed by said housing and rotor member for providing a fluid passage between a selected one of said ports and said opening in said syringe end portion upon setting said housing and rotor member in a corresponding selected operating position; and second means including detent means for setting said housing and rotor member into a selected one of a second remaining portion of said plurality of operating positions by releasing said detent means and rotating said housing relative to said rotor member, whereby the provision of a fluid passage between one of said plurality of ports corresponding to one of the second portion of said plurality of operating positions and said syringe opening solely by rotating said housing relative to said rotor member is normally prevented.

2. Intubation apparatus as recited in claim 1 wherein at least one of said plurality of ports corresponding to one of the second portion of said plurality of operating positions is releasably fluidly connected to sampling means, whereby the provision of a fluid passage between said sampling means and syringe opening requires releasing said detent means and rotating said housing relative to said rotor member.

3. Intubation apparatus as recited in claim 1 wherein said housing comprises a cup-shaped member having a bottom wall and a side wall, said side wall having a circumferentially extending upper edge surface and a substantial portion of said rotor member being contained within said housing.

4. Intubation apparatus as recited in claim 3 wherein said first and second setting means include an operator member secured to and rotatable with said rotor member in overlying relationship with said housing upper edge surface.

5. Intubation apparatus as recited in claim 4 wherein said first and second setting means include means formed on said operator member and said housing upper edge surface for releasably engaging said rotor member and said housing in one of said plurality of operating positions.

6. Intubation apparatus as recited in claim 5 wherein said engaging means include a flexible tab formed in said operator member having a downwardly projecting portion and a plurality of notches formed in said housing side wall extending downwardly from said housing upper edge surface, said plurality of notches corresponding to said plurality of operating positions, said downwardly projecting protion of said flexible tab adapted to be receivable in said notches upon relative rotation of said housing and operator member and to be automatically removeable from at least some of said notches upon continued rotation.

7. Intubation apparatus as recited in claim 6 wherein a shoulder is provided on said housing upper edge surface between a first and second portion of said plurality of notches, said first and second portion of said plurality of notches corresponding to said first and second portions of said plurality of operating positions respectively and comprises said first and second setting means respectively, said shoulder extending into and normally obstructing the path of said flexible tab member when in its normal position, whereby rotation of said housing relative to said operator member is prevented when said rotation is from a first portion operating position to a second portion operating position, unless the flexible tab is flexed upwardly out of obstructing relationship with said shoulder.

8. Intubation apparatus as recited in claim 6 wherein said notches define a plurality of housing side wall segments between adjacent pairs thereof, at least one of said segments being of greater height relative to said housing bottom wall than an adjacent segment thereby defining an upwardly extending shoulder between said adjacent segments, said shoulder extending into and normally obstructing the path of said flexible tab member when in its normal position, whereby rotation of said housing relative to said operator member is normally prevented upon said tab member coming into contact with said shoulder and rotation being permitted upon upwardly flexing said tab out of obstructing relationship with said shoulder.

9. Intubation apparatus comprising:
a syringe having an end portion including an opening communicating with the interior of said syringe; and
a valve assembly connected to said syringe end portion, including a substantially cup-shaped housing having a bottom wall and circumferentially extending side wall having an upper edge surface, a plurality of ports being formed through said housing bottom wall and spaced along an arcuate path; a rotor member rotatably disposed in said cup-shaped housing, said rotor member including a body portion having a radially extending channel formed therethrough, one end of said channel adapted to selectively move into fluid communication with said ports upon rotation of said rotor member relative to said housing, and an axially extending stem portion having a passage formed therethrough; one end of said passage communicating with the other end of said channel and the end therof communicating with said opening in said syringe end portion.

10. Intubation apparatus as recited in claim 9 further including an operator member secured to and rotatable with said rotor member in overlying relationship with said housing upper edge surface.

11. Intubation apparatus as recited in claim 10 further including means formed on said operating member and housing side wall for automatically setting said housing and rotor member into a selected operating position wherein said one end of said channel is in fluid communication with a selected one of said ports.

12. Intubation apparatus as recited in claim 11 wherein said setting means includes means for preventing inadvertent relative rotation of said rotor member and housing into a position wherein said one end of said channel is in fluid communication with at least one selected port.

13. Intubation apparatus as recited in claim 12 further including a tube structure having one end coupled to said selected port and the second end thereof is connected to a receptacle for receiving samples of material from said cavity.

14. Intubation apparatus as recited in claim 11 wherein said ports are adapted to couple tubing to said valve to provide a system for directing fluid to and from a cavity of a living body to which said apparatus is applied.

15. Intubation apparatus as recited in claim 14 further including a first tube structure having one end coupled to a first one of said ports and the second end thereof adapted to be disposed in said body cavity, a second tube structure having one end coupled to a second one of said ports and the second end thereof adapted to be in fluid communication with a source of body treatment fluid, and a third tube structure having one end coupled to a third one of ports and the second end therof adapted for connection to a waste receptacle.

16. Intubation apparatus as recited in claim 14 wherein said setting means comprises of plurality of notches, corresponding to said plurality of ports, formed in said upper edge surface of said housing side wall, and a flexible tab formed in said operator member normally biased into contact with said upper edge surface and adapted to be received in one of said notches during relative rotation of said rotor member and housing.

17. Intubation apparatus comprising:
a syringe having an end portion including an opening communicating with the interior of said syringe and
a valve assembly connected to said syringe end portion including a housing having a plurality of ports; a rotor member, said housing and rotor member being rotatably mounted with respect to each other; means for setting said housing and rotor member into a selected one of a plurality of positions relative to each other, said plurality of positions corresponding to said plurality of ports; means formed by said housing and rotor member for providing a fluid passage between a selected one of said ports and said opening in said syringe end portion upon setting said housing and rotor member in corresponding selected positions; and means for normally preventing inadvertently setting said housing and rotor member into at least one of said plurality of positions whereby an inadvertent provision of a fluid passage between at least one of said plurality of ports corresponding to said at least one of said plurality positions and said syringe opening is normally prevented.

* * * * *